(12) United States Patent
Swing

(10) Patent No.: US 6,256,539 B1
(45) Date of Patent: Jul. 3, 2001

(54) TREATMENT OF PERIPHERAL VASCULAR DISEASE, LEG CRAMPS AND INJURIES USING NEEDLES AND ELECTRICAL STIMULATION

(75) Inventor: Fred P. Swing, 24010 Harborview Rd., Charlotte Harbor, FL (US) 33980

(73) Assignee: Fred P. Swing, Port Charlotte, FL (US)

( * ) Notice: Subject to any disclaimer, the term of this patent is extended or adjusted under 35 U.S.C. 154(b) by 0 days.

(21) Appl. No.: 09/232,065

(22) Filed: Jan. 15, 1999

Related U.S. Application Data

(63) Continuation-in-part of application No. 08/864,307, filed on May 28, 1997, now Pat. No. 5,861,016.

(51) Int. Cl.[7] .................................................. A61N 1/04

(52) U.S. Cl. ........................................................... 607/50

(58) Field of Search .............................. 607/50; 128/898; 605/185, 186, 189

(56) References Cited

FOREIGN PATENT DOCUMENTS

0971328 * 11/1982 (RU) ..................................... 606/189

* cited by examiner

Primary Examiner—William E. Kamm
(74) Attorney, Agent, or Firm—Stroock & Stroock & Lavan LLP

(57) ABSTRACT

A method for healing an injury of a patient using an electrical stimulator and acupuncture needles is provided. The method can include the step of positioning a plurality of acupuncture needles coupled to the electrical stimulator at specific acupuncture points. The next step includes applying a current to the acupuncture needles. The first half of the treatment, a current is applied through the needles until a stinging sensation (or pain) is felt by the patient. Halfway through the treatment, the current is increased until a stinging sensation is again felt by the patient. At least four acupuncture needles are positioned at specific acupuncture points and alternating the polarity of the needles. The method may also include the use of Auriculotherapy, electrical stimulation without needles, in conjunction with the acupuncture needles and electric stimulator. The method may also be applied to the treatment of peripheral vascular disease, due to the effect of increasing blood flow and oxygen to the vessels.

14 Claims, 4 Drawing Sheets

TREATMENT OF PERIPHERAL VASCULAR DISEASE, LEG CRAMPS AND INJURIES USING NEEDLES AND ELECTRICAL STIMULATION

CROSS REFERENCE

This application is a continuation in part of U.S. application Ser. No. 08/864,307, filed May 28, 1997 entitled "Method of Wound Healing Using Electrical Stimulation and Acupuncture Needles", and now U.S. Pat. No. 5,861,016 the contents of which are incorporated by reference.

BACKGROUND OF THE INVENTION

This invention relates generally to a method of healing an injury, and more particularly to a method of healing an injury using electrical stimulation and/or acupuncture needles.

While electrical stimulators are well known in the art, they are typically used in conjunction with Traditional Chinese Medicine meridians ("TCM"). TCM is an ancient procedure that uses 250 different points, which are points of lesser electrical resistance on the human body, to cure various medical conditions. That is, acupuncture needles are inserted at these predetermined points on TCM meridians (lines) and then left alone for a period of time or stimulated by a variety of methods:

1. manually manipulating the needles;
2. heat applied to the needles (moxa —similar to a hot lighted end of a cigar); and
3. an electrical current.

In addition, the Craig PENS theory and treatment is well-known in the art. The PENS method follows dermatomes, myotomes and neurotomes of the human body which are found in various anatomy books. Similar to TCM, the acupuncture needles are positioned at pre-defined locations on the human body associated with specific muscles, nerves or the like to dissipate pain. Craig PENS is used for pain treatments only —back pain; neck pain; joint pain, etc.

Accordingly, prior art methods fail to teach the use acupuncture needles to heal an injury irrespective of the specific pressure points or Chinese meridian points on the human body. To overcome this deficiency, the present invention uses acupuncture needles and positions them with specific reference to the location of the injury.

Prior art methods also fail to teach the use of auriculotherapy on the ear to facilitate treatment of peripheral vascular disease, leg cramping or wounds. Auriculotherapy is performed by using either electrical stimulation or needles.

SUMMARY OF THE INVENTION

Generally speaking, in accordance with the invention, a method for healing a injury of a patient using electrical stimulation and/or needles are provided. The method includes the step of positioning a plurality of acupuncture needles at specific acupuncture points. The method also includes allowing the natural electric current present in the needles to pass a current through the acupuncture needles. At least four acupuncture needles can be positioned at specific acupuncture points. In an embodiment of the invention, the use of needles at acupuncture points or Auriculotherapy on the ear alone and/or in combination with surrounding an injured area with acupuncture needles coupled to electric stimulation are employed to treat peripheral vascular disease, leg cramps (claudicia pain) and leg wounds.

Accordingly, it is an object of the invention to provide an improved method of healing injuries using electrical stimulation and/or acupuncture needles.

Still other objects and advantages of the invention will in part be obvious and will in part be apparent from the specification.

The invention accordingly comprises the several steps and the relation of one or more of such steps with respect to each of the others thereof, which will be exemplified in the method hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3 is a schematic diagram apparatus used to heal peripheral vascular disease, leg cramping or an injury in accordance with a preferred embodiment of the invention; and.

DETAILED DESCRIPTION OF THE PREFERRED EMBODIMENTS

Figure 1:
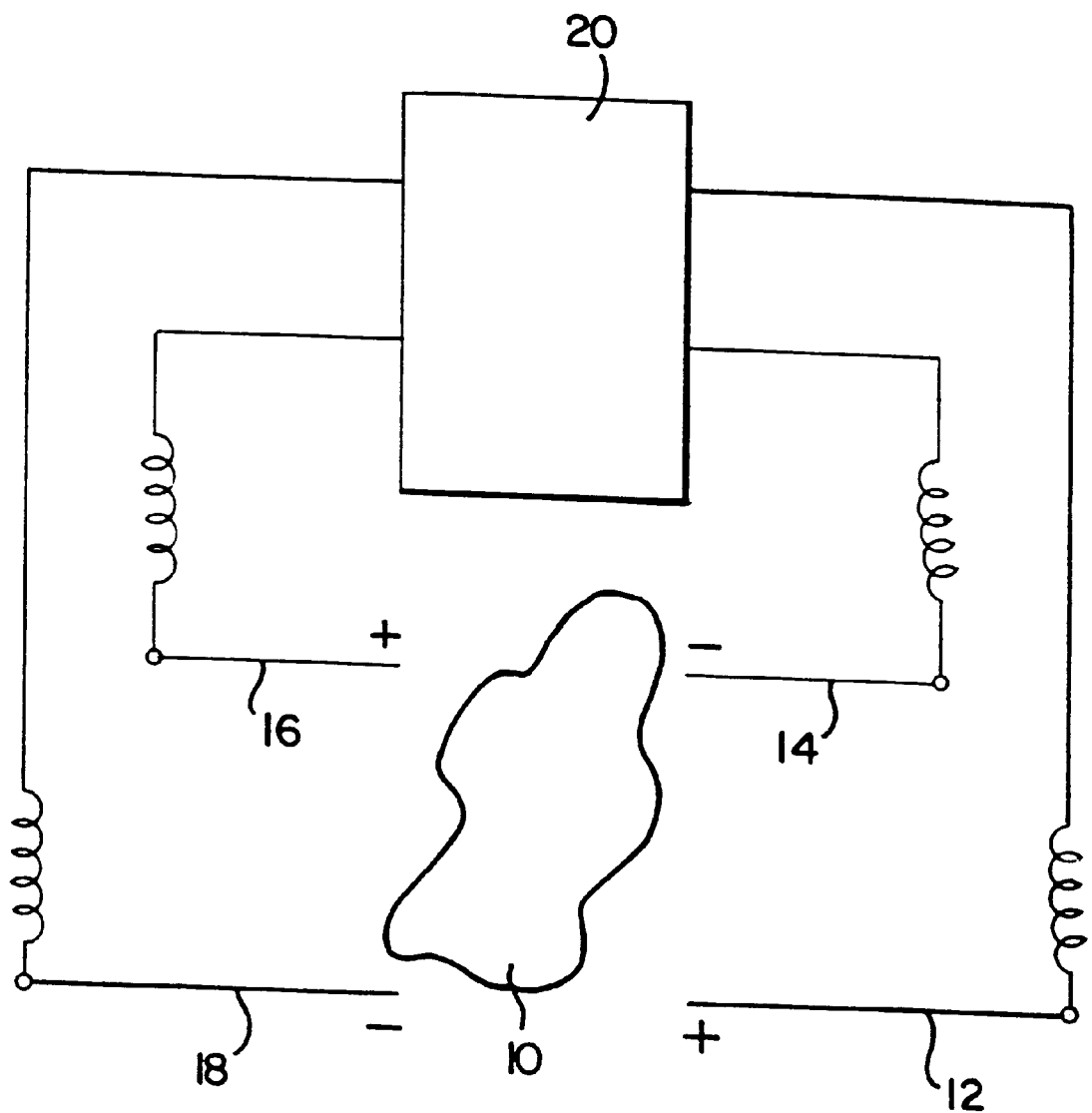
FIG. 1 is a schematic diagram of an apparatus used to heal an injury in accordance with a preferred embodiment of the invention.
Figure 2:
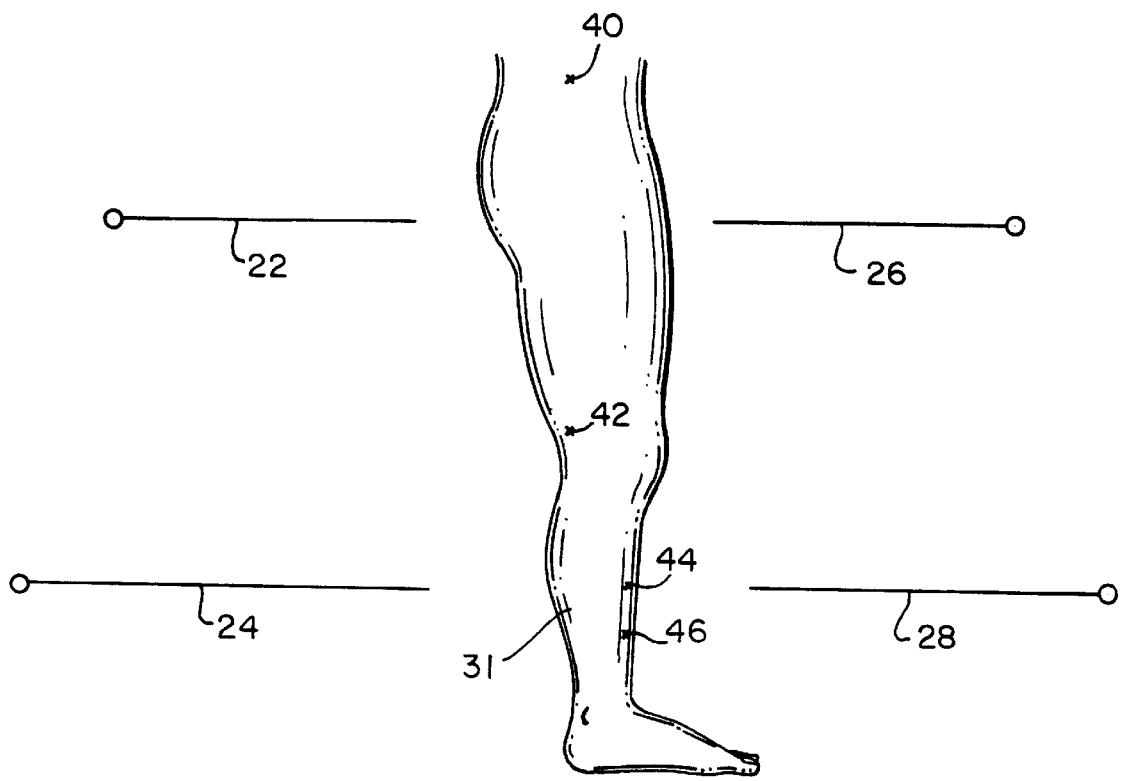
FIG. 2 is a schematic diagram of an apparatus used to heal peripheral vascular disease, leg cramping or an injury in accordance with a preferred embodiment of the invention.

A schematic diagram of an apparatus used to heal an injury using electrical stimulation is shown generally in FIG. 1. An injury 10 is substantially surrounded by acupuncture needles 12, 14, 16 and 18. While four acupuncture needles are used, any combination of needles may be used and preferably in the range of 4–8 so long as it properly encircles the injury. Needles of different polarity reside in proximity of one another so that, for example, two positive or two negative needles are not adjacent. Preferably, needles 12, 14, 16 and 18 are approximately two inches from one another and are positioned approximately ½ to two inches from injury 10. in a second embodiment of the invention, as shown in FIG. 2, needles 22, 24, 26 and 28 can be placed on the leg, on the hip or on specific acupuncture points.

Needles 12, 14, 16 and 18 are connected to an electrical acupuncture stimulator 20. Electrical acupuncture stimulators 20 are well known in the art. For example, Electrotherapeutic Devices, Inc. of Markham Ontario, Canada sells a Multiple Electronic Acupunctoscope Model G6805 and Ito Co., Ltd. of Japan sells an Electropuncture IC1107 model. Electrical stimulator 20 is designed for clinical use and transmits pulsating currents of different intensities and frequencies through the acupuncture needles to the human body.

Electrical stimulator 20 is coupled to needles 12, 14, 16 and 18 alternating between the positive and negative leads so that a positive needle does not reside immediate adjacent to a negative needle and vice versa. Traditional acupuncture lines such as traditional Chinese meridians may also be used as described in the second embodiment of the invention. As set forth above, the needle placement may be based solely on the size of the injury and the positioning of the various needles with respect to one another or the needles may be placed on the leg, hip or specific acupuncture points.

To treat peripheral vascular disease or an injury, electrical stimulator 20 is turned on and the frequency of the current is increased until the needles sting or begin to hurt the patient. At this point the frequency is held constant. A two to four hertz frequency is preferably used to apply the current. The size of the current depends on the frequency of the electrical stimulator being used, which is preferably in the range of 1 Hz to 25 Hz. Any frequency in the range of preferably one to twenty-five Hz may be used depending on the individual, the size of the injury and other such issues.

Halfway through the treatment, which generally lasts 20 to 30 minutes, the frequency of the current is again increased until it starts to sting or begins to hurt the patient and at this point the frequency is held constant. The above method should be repeated 3–5 times a week. Treatments are preferably continued until the peripheral vascular disease is cleared, the leg pain subsides, or injury healing is complete or almost complete in smaller injuries or until in bigger injuries the injury bed has enough granulation tissue (growth of blood vessels) covering the injury so a skin graft can be done. After the skin graft is done, acupuncture treatments may be continued for 1–2 weeks to increase graft survival.

It has been determined that peripheral vascular disease can cause a reduction in blood flow, and thus oxygen and nutrients to the vessels. Peripheral vascular disease can in turn cause leg cramping and/or inhibit injuries from healing.

Based on the application of the current to the blood vessels in the vicinity of the injury, the blood flow is likely to be increased to the vessels or to the injury, thereby decreasing the healing time. By increasing the blood flow in and around the area of the injury, more oxygen and body nutrients can get to the injury, thereby allowing the injury to heal much quicker. This can also change non-healing injuries to healing injuries. Increasing the blood flow in a leg suffering from leg cramps makes it possible for more oxygen and body nutrients to get to the blood vessels thereby alleviating leg cramping.

In a second embodiment of the invention, as shown in FIG. 2, at least four acupuncture needles 22, 24, 26, 28, are placed on the hip, leg 31 or in specific acupuncture locations 40,42,44,46. If treating a leg injury or an ulcer, peripheral vascular disease or leg cramping, four needles 22, 24, 26, 28, can be positioned at specific acupunture locations 40, 42, for example, Stomach 30, Stomach 34, Spleen 8 and Kidney 9 allowing the natural current present in the needles to pass a current through the needles into the body at the specific points of insertion. As described above, this can blood flow to the vessels, thus treating peripheral vascular disease, leg cramping and can speed healing of a leg wound.

Figure 3:
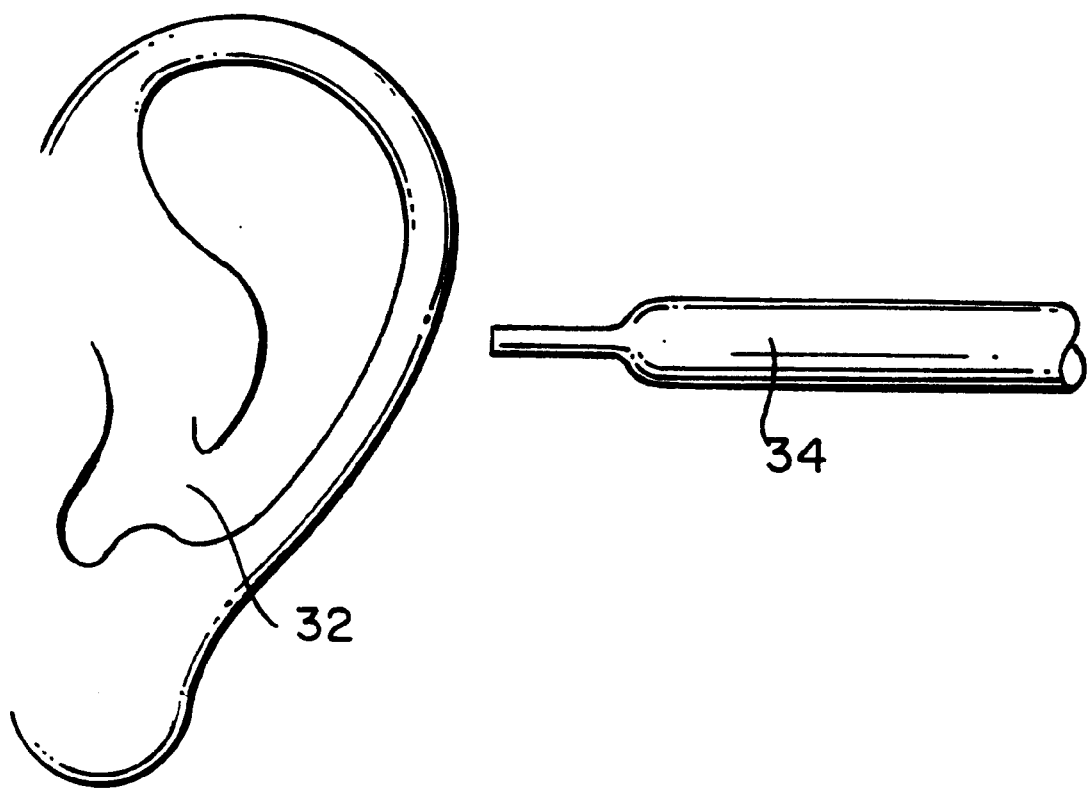

In a third preferred embodiment of the invention, the use of Auriculotherapy, which uses electric stimuli without the use of needles, can be used to treat peripheral vascular disease, leg cramps or injuries. As similarly described above, the use of electrical stimulation generally increases blood flow and oxygen to the vessels. As shown in FIG. 3, the use of Auriculotherapy is applied to the ear on the side of the affected limb. (e.g. right leg, right ear). An Auriculotherapy device 33 can be applied to known points in or on the ear which can stimulate another region of the body. For example, when treating a leg injury, a red dot will commonly appear in a patient's ear 32, corresponding to the affected leg. Auriculotherapy can be used to stimulate points as described in *Auriculotherapy Manual, Chinese and Western Systems of Ear Acupuncture*, Perry Olson, PhD(2d ed. 1996). Auriculotherapy stimulation can be applied to a red dot or red streak which often represents the site of the injury on the affected limb, in order to help stimulate blood flow to the affected area and thus facilitate healing. Additionally, TCM medicine can be used to facilitate healing of the injury in the following fashion. Phase One, Phase Two and Phase Three Lung Points in the ear can be used to facilitate healing of the skin of the wound. Phase One, Phase Two and Phase Three Spleen Points can be used to facilitate healing the tissue under the skin. If a tendon is involved in the wound, Phase One and Phase Two of the Liver Points can be used to facilitate healing of the tendons.

In a fourth preferred embodiment of the invention, a combination of the first or second embodiment with the third embodiment, four points of stimuli can be used in conjunction with Auriculotherapy on the ear. If treating a leg injury or an ulcer, peripheral vascular disease or leg cramping, four needles can be positioned at for example, Stomach 30, Stomach 34, Spleen 8 and Kidney 9. Then, Auriculotherapy, which uses only electric stimulation without needles, can be applied to the ear of whichever leg is involved (e.g. right leg, right ear). As described in connection with the other embodiments, the application of this treatment method should increase the flow of blood, bringing more oxygen to the vessels, thus increasing the rate of injury healing. Auriculotherapy in the ear can stimulate dispersion when applied at 10 Hz over a period of approximately 24 seconds or more and from 10 to 40 microamps.

Figure 4:
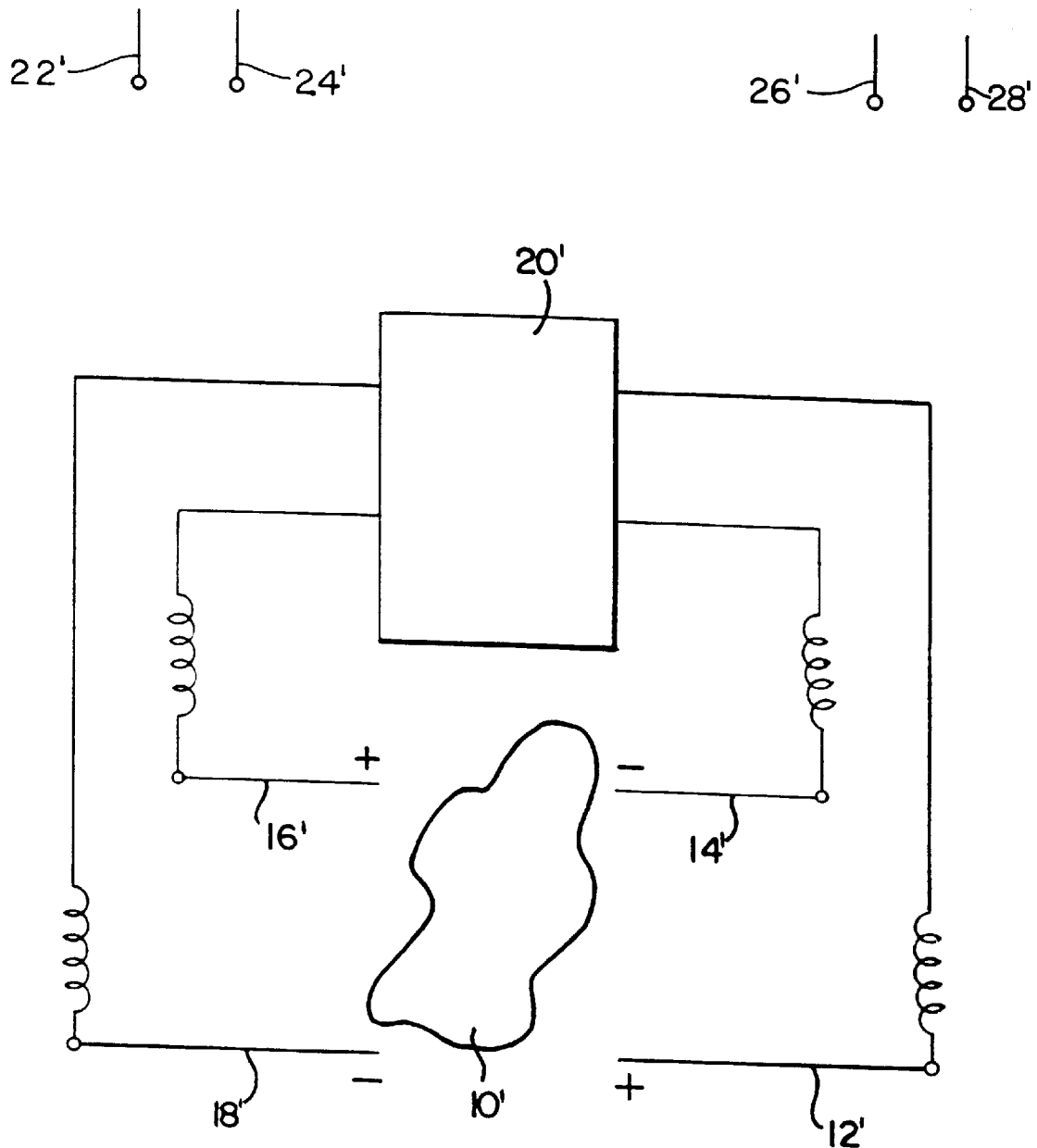
FIG. 4 is a schematic diagram apparatus used to heal peripheral vascular disease, leg cramping or an injury in accordance with a preferred embodiment of the invention.

In a fifth preferred embodiment, as depicted in FIG. 4, a combination of the first and second preferred embodiments, Electrical stimulator 20' is coupled to needles 12', 14', 16' and 18'. Needles 12', 14', 16' and 18' are positioned substantially around the injury 10'. Needles 22', 24', 26' and 28' are positioned at points on the leg, hip or specific acupuncture points. The combination of different needles providing electric stimuli can increase blood flow increasing the rate of healing of the injury.

In a sixth preferred embodiment, the third and fourth embodiments are combined in treating an injury. Electrical stimulator 20' is coupled to needles 12', 14', 16' and 18'. Needles 12', 14', 16' and 18' are positioned substantially around the injury. Needles 22', 24', 26' and 28'are positioned at points on the leg, hip or specific acupuncture points. Auriculotherapy are applied to the ear of the affected limb. The combination of different electric stimuli can increase blood flow increasing the rate of healing of the injury.

EXAMPLE

An individual sustained an insect bite on the lower left leg. The injury appeared as a two centimeter, red, raised area with a fluid-center approximately one centimeter in size. After three days, it was opened and drained. Thereafter, the red area enlarged to five centimeters in size and the pain increased at the injury site and spread to cover the leg area from the knee down to the ankle. The injury was treated with normal saline rinse and clean dry dressing twice a day. The necrotic center gradually enlarged. Five days after the initial bite, the patient started taking Augmentin and Dapsone orally prescribed by a physician. Three days thereafter the pain was increasing and was interfering with walking.

Seven days from the original bite, another doctor initiated an IV Vancomycin for twelve days with whirlpool and debridement by physical therapy. Three days later, celulitis set in and the patient was restarted on IV Vancomycin for five days. More than a month later, while the celulitis and infection cleared up, the injury remained open with no further healing. Shortly thereafter, the ulcer (injury) was two to three millimeters deep and the diameter was approximately 2 ½ to 3 centimeters. The patient had indicated that there had been no change in the size of the ulcer for more than three weeks.

As a result, the method of the first embodiment of the invention, described above, was employed in which four needles 12, 14, 16 and 18 were placed around the injury, with alternating polarity separating each needle. The needles were spaced two inches apart from one another and were positioned ½ to 2 inches away from the injury. Electrical stimulator 20 was activated using a frequency of 4 hertz. A current was applied until a stinging pain was felt by the patient. Halfway through the treatment, approximately ten minutes into the treatment, the current was increased until a stinging pain was again felt by the patient. This process lasted approximately 20 minutes in total. As a result of the application, the cyanotic (blue) rim around the injury became pink and 12 hours after the first acupuncture treatment 95% of the pain disappeared.

By the fourth treatment which occurred seven days after the original treatment, the ulcer diameter had decreased by two millimeters and the entire base of the injury (ulcer) had filled in with granulation tissue. In another 5 days, a scab formed over the injury and in another 5 days the scab fell off —the injury (ulcer) completely healed 17 days from the first acupuncture treatment. Based on the application of the method described above, the treatment destroyed the toxin from the bite and broke up the Vasospasm (constricted blood vessel) on the rim of the ulcer, thus allowing the ulcer to heal.

The same method may be used as described above, for non-healing skin ulcers, diabetic non-healing skin ulcers and peripheral vascular disease non-healing skin ulcers and or any skin injury not healing due to decreased blood flow in the area of the injury.

The method of treating an injury using needles and electrical stimulation described as taught in connection with either the second or fifth may also be used in the treatment of peripheral vascular disease. The use of needles and electric stimulation increases blood flow and brings more oxygen to the vessels.

The method of treating an injury using needles and electrical stimulation may also be used in conjunction with Auriculotherapy applied to the ear described as in connection with the third, fourth or sixth embodiments. When treating a leg injury or an ulcer, four needles can be positioned at for example the following known acupuncture points, Stomach 30, Stomach 34, Spleen 8 and Kidney 9. The needle positioned at Stomach 30 should be located two cuns lateral to the superior border of the pubic bone. The needle positioned at Stomach 34 should be positioned in a depression, two cuns proximal to the lateral superior border of the patella. The needle positioned at Spleen 8 should be on the medial side of the tibia, three cuns below the tibial plateau. The needle positioned at Kidney 8 should be on the medial side of the tibia, two cuns above Kidney 3 and one cun medial to Kidney 7. Then, Auriculotherapy, which uses only electric stimulation without needles, can be applied to the ear of whichever leg is involved (e.g. right leg, right ear). The application of this treatment method generally increases the flow of blood, bringing more oxygen to the vessels, thus increasing the rate of injury healing.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method of treating an ailment of a limb of a patient using acupuncture needles, comprising the steps of:

positioning a plurality of acupuncture needles at specific acupuncture points on the leg and hip, wherein the specific acupuncture points are stomach 30, stomach 34, spleen 8 and kidney 9.

2. The method of claim 1, wherein the ailment is leg cramping.

3. The method of claim 1, wherein the ailment is a wound.

4. The method of claim 1 wherein the ailment is peripheral vascular disease.

5. A method of treating an ailment of a limb using auriculotherapy comprising the steps of:

applying electrical stimulation to a selected spot in the ear associated with the ailment of the limb.

6. The method of claim 5, wherein the ailment is leg cramping.

7. The method of claim 5, wherein the ailment is a wound.

8. The method of claim 5, wherein the ailment is peripheral vascular disease.

9. The method of claim 5, wherein auriculotherapy is applied to the ear on the side of the limb as that which contains the ailment.

10. The method of claim 5, wherein stimulation is applied to the selected spot in the ear indicated by a red dot or red streak.

11. The method of claim 5, further comprising the step of positioning a plurality of acupuncture needles at specific acupuncture points on the leg and hip, wherein the specific acupuncture points are stomach 30, stomach 34, spleen 8 and kidney 9.

12. The method of claim 5, further comprising the step of applying Traditional Chinese Medicine to Phase One, Phase Two and Phase Three Lung Points in the ear wherein healing of the skin of a wound is facilitated.

13. The method of claim 5, further comprising the step of applying Traditional Chinese Medicine to Phase One, Phase Two and Phase Three Spleen Points in the ear wherein healing of the tissue under the skin of the wound is facilitated.

14. The method of claim 5, further comprising the step of applying Traditional Chinese Medicine to Phase One, Phase Two and Phase Three Liver Points in the ear wherein healing of the tendons is facilitated.

* * * * *